United States Patent
Fawzi et al.

(10) Patent No.: US 10,188,843 B2
(45) Date of Patent: *Jan. 29, 2019

(54) ULTRASOUND AND MICROBUBBLES IN OCULAR DIAGNOSTICS AND THERAPIES

(71) Applicant: Doheny Eye Institute, Los Angeles, CA (US)

(72) Inventors: Amani Fawzi, Los Angeles, CA (US); Hossein Ameri, Alhambra, CA (US); Mark S. Humayun, Glendale, CA (US)

(73) Assignees: UNIVERSITY OF SOUTHERN CALIFORNIA, Los Angeles, CA (US); DOHENY EYE INSTITUTE, Los Angeles, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/453,150

(22) Filed: Mar. 8, 2017

(65) Prior Publication Data

US 2018/0021557 A1 Jan. 25, 2018

Related U.S. Application Data

(63) Continuation of application No. 14/278,320, filed on May 15, 2014, now abandoned, which is a
(Continued)

(51) Int. Cl.
*A61M 37/00* (2006.01)
*A61B 3/12* (2006.01)
(Continued)

(52) U.S. Cl.
CPC ....... *A61M 37/0092* (2013.01); *A61B 3/1233* (2013.01); *A61B 8/06* (2013.01);
(Continued)

(58) Field of Classification Search
CPC ... A61M 31/00; A61M 37/0092; A61B 8/483; A61B 8/10; A61B 8/481; A61B 8/08;
(Continued)

(56) References Cited

U.S. PATENT DOCUMENTS

2001/0008880 A1* 7/2001 Porter .................. A61K 9/5052
424/490

* cited by examiner

*Primary Examiner* — Bo Joseph Peng
(74) *Attorney, Agent, or Firm* — Yakov S. Sidorin; Quarles & Brady LLP

(57) ABSTRACT

The present disclosure described methods, systems, and techniques for applying contrast-enhanced ultrasound to locate areas of blockage within retinal vessels and to break up clots that are causing damage. In addition to identifying the damaged area, the researchers anticipate that the initial image may serve as a baseline for monitoring the effect of treatment on the vessel, which may be achieved in multiple ways. The vibration effect of the ultrasound itself may suffice to dislodge clots. The microbubbles may also be coated or filled with medication, with ultrasonic shock waves activating the coating or causing mini explosions to release the medicine. Loading the microbubbles with a therapeutic agent, visualizing their presence at the diseased site using the ultrasound diagnostic mode, and then activating the microbubbles to release their contents at the targeted lesion could be a powerful and effective way to reverse occlusion without harming other areas of the eye or body.

16 Claims, 3 Drawing Sheets

Related U.S. Application Data continuation of application No. 12/186,640, filed on Aug. 6, 2008, now Pat. No. 8,764,658, which is a continuation-in-part of application No. 12/102,293, filed on Apr. 14, 2008, now Pat. No. 8,684,935, which is a continuation-in-part of application No. 12/061,147, filed on Apr. 2, 2008, now abandoned, and a continuation-in-part of application No. 12/061,120, filed on Apr. 2, 2008, now abandoned.

(60) Provisional application No. 61/030,075, filed on Feb. 20, 2008, provisional application No. 60/911,385, filed on Apr. 12, 2007, provisional application No. 60/909,496, filed on Apr. 2, 2007, provisional application No. 60/909,522, filed on Apr. 2, 2007, provisional application No. 61/030,075, filed on Feb. 20, 2008, provisional application No. 60/911,385, filed on Apr. 12, 2007, provisional application No. 60/909,522, filed on Apr. 2, 2007, provisional application No. 60/909,496, filed on Apr. 2, 2007.

(51) Int. Cl.

| | | |
|---|---|---|
| *A61B 8/06* | (2006.01) | |
| *A61B 8/12* | (2006.01) | |
| *A61B 8/13* | (2006.01) | |
| *A61B 8/00* | (2006.01) | |
| *A61B 8/10* | (2006.01) | |
| *A61B 8/08* | (2006.01) | |
| *A61K 41/00* | (2006.01) | |
| *A61K 49/22* | (2006.01) | |
| *A61M 31/00* | (2006.01) | |
| *A61N 7/00* | (2006.01) | |
| *A61F 9/008* | (2006.01) | |
| *A61K 38/00* | (2006.01) | |

(52) U.S. Cl.
CPC ............... *A61B 8/10* (2013.01); *A61B 8/12* (2013.01); *A61B 8/13* (2013.01); *A61B 8/4488* (2013.01); *A61B 8/481* (2013.01); *A61B 8/483* (2013.01); *A61K 41/0014* (2013.01); *A61K 49/223* (2013.01); *A61M 31/00* (2013.01); *A61N 7/00* (2013.01); *A61B 8/08* (2013.01); *A61F 9/008* (2013.01); *A61F 2009/00863* (2013.01); *A61K 38/00* (2013.01); *G01N 2203/0076* (2013.01); *G01N 2203/0658* (2013.01)

(58) Field of Classification Search
CPC ........... A61B 3/1233; A61B 8/06; A61B 8/12; A61B 8/13; A61B 8/4488; A61K 41/0014; A61K 49/223; A61K 38/00; A61N 7/00; A61F 9/008; A61F 2009/00863; G01N 2203/0658; G01N 2203/0076
See application file for complete search history.

ULTRASOUND AND MICROBUBBLES IN OCULAR DIAGNOSTICS AND THERAPIES

RELATED APPLICATIONS

This application is a continuation-in-part of related U.S. patent application Ser. No. 12/061,147 filed 2 Apr. 2008 and entitled "Preoperative and Intra-Operative Lens Hardness Measurement by Ultrasound," which claims the benefit of U.S. Provisional Patent Application No. 60/909,496 filed 2 Apr. 2007; this application also is a continuation-in-part of U.S. patent application Ser. No. 12/061,120 filed 2 Apr. 2008 and entitled "Thrombolysis In Retinal Vessels with Ultrasound," which claims the benefit of U.S. Provisional Patent Application No. 60/911,385 filed 12 Apr. 2007; this application is a continuation-in-part of U.S. patent application Ser. No. 12/102,293 filed 14 Apr. 2008 and entitled "Intraocular Doppler Techniques," which claims the benefit of U.S. Provisional Patent Application No. 60/911,385 filed 12 Apr. 2007; this application claims the benefit of U.S. Provisional Patent Application No. 61/030,075 filed 20 Feb. 2008 and U.S. Provisional Patent Application No. 60/954,129 filed 6 Aug. 2007; the entire contents of all of which applications are incorporated herein by reference.

BACKGROUND

There is presently no cure for retinal vascular occlusion, the blockage of blood flow by clots in central or branch retinal veins and arteries that causes vision loss and blindness. Yet unlike other blinding retinal diseases such as macular degeneration and retinitis pigmentosa, for which definitive treatments remain years if not decades away, a cure for retinal vascular occlusions could be obtained within as little as one to two years. This is good news for the relatively large number of people—as many as 2 to 4 percent of people over age 70 (51% of cases of retinal vascular occlusion occur over age 65) T/K—who are affected by this disorder.

A cure for retinal vessel occlusion could be achieved by removing the blood clot. Clot-dissolving drugs that enter the bloodstream, however, may provoke life-threatening complications, and surgical intervention and injections directly to the eye have had limited success. Current treatments for such occlusions are therefore limited to laser applications that treat complications rather than the condition itself. For example, laser is applied to patients with poor blood flow in the eye secondary to retinal vessel occlusions, leading to growth of new vessels in the front of the eye and increased eye pressure. At that point the laser only serves stop new blood vessel growth, but does not help to recover lost vision or improve blood flow.

Current treatments for vein occlusions are limited to laser application to prevent complications or invasive surgical therapies that have limited success. The primary disease process involves a blood clot in the vein. Currently there is no definite treatment for retinal vascular occlusive diseases such as central or branch retinal vein occlusion and central or branch retinal artery occlusion. A cure in these conditions would involve removal of the blood clot. Systemic use of thrombolytics (drugs that dissolve the blood clot) may be associated with life threatening complications; on the other hand, intravitreal injection of these drugs has proved to be ineffective.

SUMMARY

Embodiments of the present disclosure can provide the ability to dissolve a blood clot (e.g., such as one in the eye) by utilization of ultrasound and contrast agents, known as microbubbles. In addition, microbubble enhancement and targeted therapies using ultrasound according to the present disclosure can provide the ability to deliver targeted therapies in the eye and elsewhere in patients.

Drug delivery approaches to the eye are currently focused on invasive surgical implants, with the attendant risks and complications. The ability to image, while treating, vascular disease of the eye using targeted microbubbles is a great advantage permitting direct observation of the microbubbles and their targeted activation at the site of disease.

Because of the eye being especially sequestered and being a superficial organ, embodiments of the present disclosure can provide an exceptional opportunity to deliver drugs without systemic side effects. For example, by attaching the required medications to the microbubbles and then delivering ultrasound to the exact location in the eye where the drug is needed, targeting is achieved.

Removal of a blood clot using microbubble enhanced ultrasound thrombolysis can have a long lasting and curative effect on this disease. Other ocular diseases that can benefit from microbubble targeting include macular degeneration. For such, microbubbles cab be loaded with a specific therapeutic agent that is released only at the target lesion/region.

Moreover, such approaches/embodiments can be very successful in drug delivery of anti-cancer medications to tumors inside the eye, such as retinoblastoma in children.

Chemotherapeutic agents for retinoblastoma have a large number of systemic side effects that can be devastating, and if we are able to deliver the drug only to the tumor, with direct visualization and confirmation of delivery using ultrasound and targeted microbubbles, this would have a great effect on the efficacy of the therapy as well as limit the systemic complications.

Image guided interventions using these microbubbles according to the present disclosure can be applied to various ocular diseases with abnormal or aberrant vascularization, including neovascular macular degeneration, diabetic retinopathy, corneal neovascularization, and the like.

Aspects/embodiments of the present disclosure can also help in delivering chemotherapeutic drugs to vascular intraocular tumors while sparing the rest of the ocular structures. By focusing the ultrasound on the abnormal tissue, the chemotherapeutics attached to the microbubbles can be delivered directly to the tumor, while sparing other areas of the eye and the rest of the body.

Other features and advantages of the present disclosure will be understood upon reading and understanding the detailed description of exemplary embodiments, described herein, in conjunction with reference to the drawings.

BRIEF DESCRIPTION OF DRAWINGS

Aspects of the disclosure may be more fully understood from the following description when read together with the accompanying drawings, which are to be regarded as illustrative in nature, and not as limiting. The drawings are not necessarily to scale, emphasis instead being placed on the principles of the disclosure. In the drawings.

Figure 1:
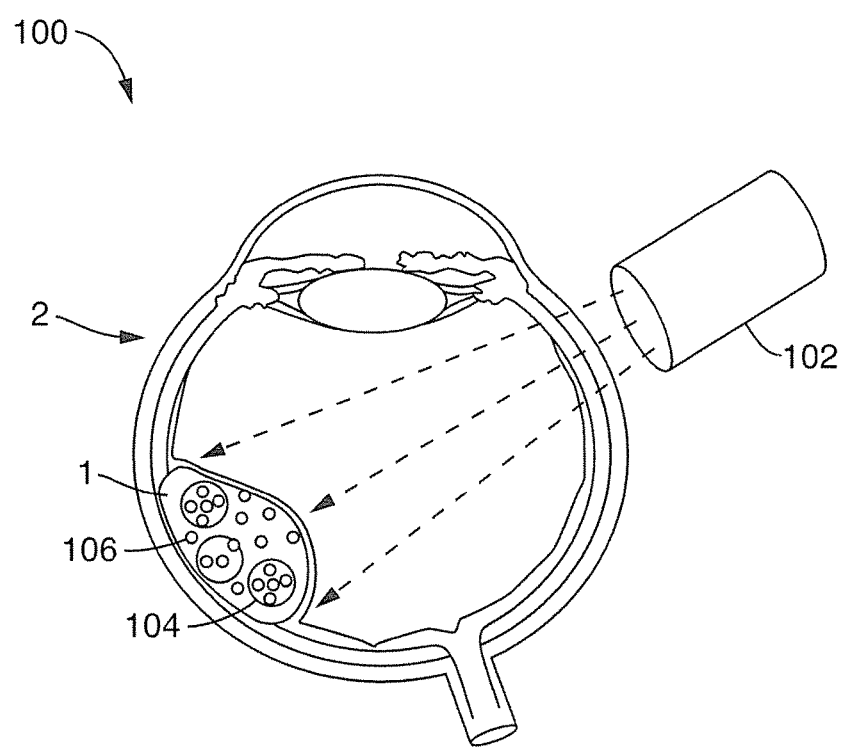
FIG. 1 depicts application of ultrasound energy from an ultrasound probe systems to release drugs from microbubbles to effect treatment of a tumor, e.g., as located in a patient's eye, in accordance with exemplary embodiments of the present disclosure.

While certain embodiments are depicted in the drawings, one skilled in the art will appreciate that the embodiments depicted are illustrative and that variations of those shown, as well as other embodiments described herein, may be envisioned and practiced within the scope of the present disclosure.

DETAILED DESCRIPTION

Aspects of the present disclosure combine ultrasound with ultrasound contrast agents, known as microbubbles, to treat selected regions of a patient by what the inventors refer to as "Contrast Enhanced Ultrasound Therapy."

Microbubbles are tiny, gas-filled lipid, or fat, bubbles that can be injected into the bloodstream, where they remain inactive unless stimulated. In conjunction with the utilization of such microbubbles, aspects and embodiments of the present disclosure utilize ultrasonic energy or ultrasound. High-frequency ultrasound has been used to create images of bone, tissue and other structures within the body by measuring the speed and intensity with which sound waves bounce off these objects and return as an echo. Ultrasound waves directed at microbubbles cause them to vibrate and return a unique echo within the bloodstream that produces a dramatic distinction, or high "contrast," between blood vessels and surrounding tissue, thus enabling clinicians to visualize areas of restricted blood flow. Specialized Doppler ultrasound, which measures the rate and volume of blood flow, can further pinpoint the extent and severity of blockage caused by blood clots.

Embodiments of the present disclosure utilize contrast-enhanced ultrasound to locate areas of blockage within retinal vessels and to break up clots that are causing damage. In addition to identifying the damaged area, the researchers anticipate that the initial image may serve as a baseline for monitoring the effect of treatment on the vessel, which may be achieved in multiple ways. The vibration effect of the ultrasound itself may suffice to dislodge clots.

The microbubbles may also be coated or filled with medication, with ultrasonic shock waves activating the coating or causing mini explosions to release the medicine. Loading the microbubbles with a therapeutic agent, visualizing their presence at the diseased site using the ultrasound diagnostic mode, and then activating the microbubbles to release their contents at the targeted lesion/region can be a powerful and effective way to reverse occlusion without harming other areas of the eye or body.

FIG. 1 depicts application 100 of ultrasound energy from an ultrasound probe system 102 to microbubbles 104 containing desired drugs 106 to effect treatment of a tumor 1 located in an eye 2, in accordance with exemplary embodiments of the present disclosure. Gas filled microbubbles (e.g., on the order of microns in size/diameter) can be visualized or imaged by ultrasound. Using specially designed probes, which have the ability to image and also activate the microbubbles, targeted therapies can be effected in the eye, while minimizing collateral damage. Such a probe is described in co-owned and co-pending U.S. patent application Ser. No. 12/061,120 filed 2 Apr. 2008 and entitled "Thrombolysis In Retinal Vessels with Ultrasound," incorporated in its entirety herein by reference. A pulsed-wave Doppler system with a PMN-PT needle transducer has been developed to measure the blood flow velocity in selected retinal vessels. See, e.g., Emanuel J. Gottlieb, et al., "PMN-PT High Frequency Ultrasonic Needle Transducers for Pulsed Wave Doppler In The Eye," 2005 IEEE Ultrasonics Symposium (IEEE 2005), the contents of which are incorporated herein by reference in their entirety.

Ultrasonic techniques have also been utilized in surgical procedures on the eye for imaging structure and/or tissue of a surgical site. See, e.g., U.S. Pat. No. 6,676,607 to de Juan, Jr. et al., the contents of which are incorporated herein by reference in their entirety.

Procedures/techniques according to the present disclosure, e.g., as depicted and described for FIG. 1, can be expanded to other ocular disorders as well. The same techniques may also be applied to ocular tumors, such as retinoblastoma in children, for which systemic treatment is associated with potentially devastating side effects, but for which drugs delivered directly to the tumor could be safe and very effective. The same principle may also apply to tumors in other parts of the body such as breast, kidney, liver, brain etc.

Moreover, the tumor does not have to have a blood clot (and they usually don't). The ultrasound breaks up the microbubbles and results in the release of the drug they carry. As long as the drug is loaded on the microbubble it does not have any effect (good or bad). The ultrasound enables one to focally release the drug in the tumors or other desired location. As a result, there is a high concentration of the active drug in the tumor or location (e.g., a clot) for destruction of such. Despite the presence of the drug in the blood, however, the other tissues in the body are spared because the drug is attached to the microbubbles and is inactive. The drug delivery for tumors can be independent of the presence of a blood clot.

Figure 2:
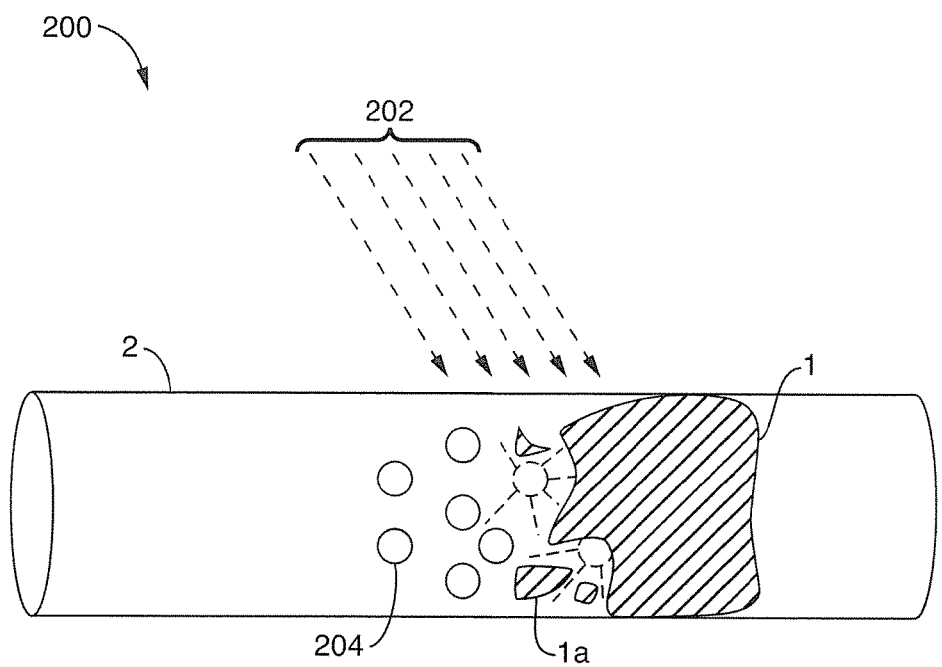
FIG. 2 depicts a application of ultrasound energy (beam) from an external or intraocular probe to an area of blockage within a retinal vessel and at a location including microbubble contrast agents, according to an exemplary embodiment of the present disclosure.

FIG. 2 depicts a application 200 of ultrasound energy (or beam) 202 from a ultrasound source, e.g., an external or intraocular probe, to an area or volume of blockage 1 within a retinal vessel 2 and at a location including microbubble contrast agents 204, according to an exemplary embodiment of the present disclosure.

The gas filled microbubbles 204 can be easily visualized using the ultrasound probe. Exemplary imaging or visualization techniques are described in co-owned and co-pending U.S. patent application Ser. No. 12/061,147 filed 2 Apr. 2008 and entitled "Preoperative and Intra-Operative Lens Hardness Measurement by Ultrasound"; U.S. patent application Ser. No. 12/061,120 filed 2 Apr. 2008 and entitled "Thrombolysis In Retinal Vessels with Ultrasound"; and U.S. patent application Ser. No. 12/102,293 filed 14 Apr. 2008 and entitled "Intraocular Doppler Techniques"; the contents of all of which are incorporated herein by reference.

The microbubbles 204 can be ruptured or "activated" to release their content by slightly altering the ultrasound mode. By "loading" these microbubbles with a specific therapeutic agent, visualizing their presence at the diseased area, and then activating the microbubbles to release their contents at the target lesion, side effects of this therapeutic agent can be limited by delivering it only to the needed site (or substantially so).

Moreover, the use of ultrasound and microbubbles in itself has the potential to dislodge blood clots, as shown in FIG. 2, with empty microbubbles rupturing and dislodging broken pieces of blood clots 1a after application of suitable ultrasound energy 202. By visualizing the microbubbles, and then activating them inside the diseased blood vessel at the site of the clot, therapy for retinal vascular occlusions can be effected.

Figure 3:
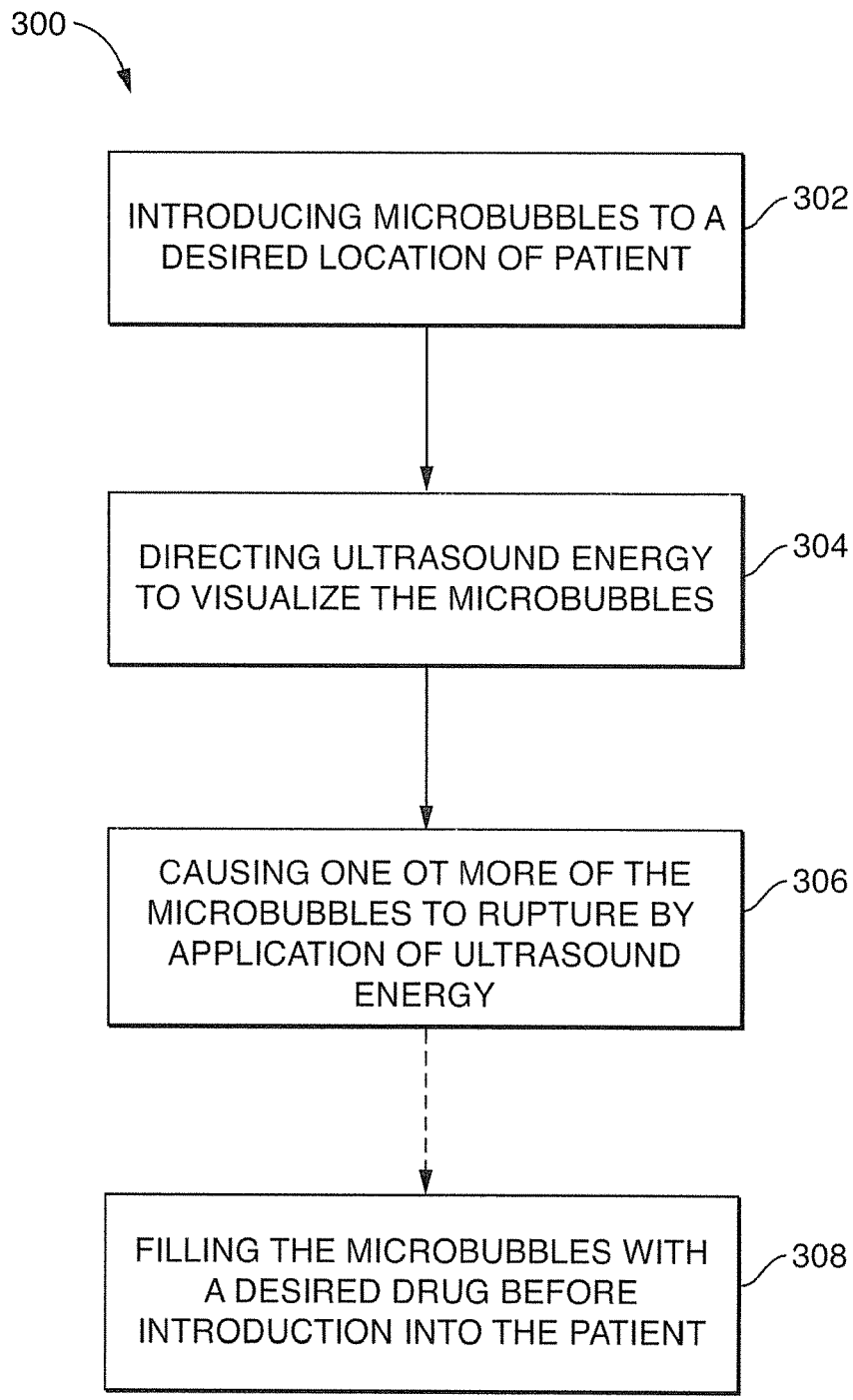
FIG. 3 depicts a block diagram of a method 300 of therapy with microbubbles in accordance with exemplary embodiments of the present disclosure.

FIG. 3 depicts a block diagram of a method 300 of therapy with microbubbles in accordance with exemplary embodiments of the present disclosure. For method 300, a desired quantity/volume of microbubbles can be introduced to a desired location of a patient, as described at 302. For example, microbubbles can be injected into the eye (vitreous cavity, subretinal, or anterior chamber) or may be injected intravascularly. Ultrasound techniques can be used to image or visualize the microbubbles at the desired location in the patient, as described at 304.

Continuing with the description of method 300, suitable ultrasound energy can be applied to the microbubbles to cause them to rupture or activate (meaning cause them to release drugs), as described as 306. In exemplary embodiments, the microbubbles can be filled or loaded with a desired drug before introduction into the patient as described at 308.

In exemplary embodiments, method 300 can include: using an ultrasound system configured and arranged to produce an ultrasound output; and supplying ultrasound contrast agents configured and arranged as microbubbles to a tumor wherein the microbubbles are loaded with chemotherapeutic drug that is active against the tumor, and wherein the ultrasound is used to localize the tumor and activate the microbubbles within the tumor to visualize and activate the release of drug within the tumor. The treated tumor can be an intraocular choroidal melanoma, and the drug can be labeled to attach to the blood vessels of the tumor selectively. The tumor can be a ciliary body melanoma or a retinoblastoma or an iris tumor. The microbubbles can be loaded with a therapeutic agent active against subretinal-neovascularization in the back of the eye.

The drug/s inside the microbubbles can, in exemplary embodiments, be labeled to attach to the blood vessels of newly formed blood vessels, and the ultrasound output is used to activate the microbubbles focally to release the therapeutic agent. An optically labeled microbubble can be loaded with a therapeutic agent and visualized optically, then activated by ultrasound to release the therapeutic agent within the subretinalneovascular complex. The microbubbles can be loaded with genetic material. The method of claim 24, wherein the disease is retinitis pigmentosa and the genetic material is able to correct the genetic defect. The treated disease can be diabetic retinopathy, and the drug or genetic material can reverse the vascular defect in abnormal blood vessels of the diseased retina. The drug can be labeled to attach to the optic nerve, and the ultrasound output can be used to activate the microbubbles focally to release the therapeutic agent. The therapeutic agent can be a nerve growth factor or a vascular growth factor or an anti-cancer agent against an optic nerve tumor.

The ultrasound energy can be applied externally from outside the eye globe or internally from inside the eye. The treatment can be directed at the cornea, the front most layer of the eye. The treatment enhances therapy of corneal disease. The microbubbles can contain a therapeutic agent against a corneal disease or infection. The microbubbles can be applied to the surface(s) of the eye that is/are loaded with drugs and the ultrasound treatment facilitates entry of the drug(s) into the anterior chamber of the eye, delivering therapeutics to the interior of the eye.

While certain embodiments have been described herein, it will be understood by one skilled in the art that the methods, systems, and apparatus of the present disclosure may be embodied in other specific forms without departing from the spirit thereof.

Accordingly, the embodiments described herein, and as claimed in the attached claims, are to be considered in all respects as illustrative of the present disclosure and not restrictive.

What is claimed is:

1. A method of treating a retinal blood vessel blockage of a patient, the method comprising:
   applying first ultrasound energy generated by an ultrasound probe to locate an area of blockage within a retinal blood vessel;
   directing gas-filled microbubbles to the area of blockage within the retinal blood vessel, wherein the microbubbles are not loaded with a therapeutic agent; and
   breaking up clots that are causing blockage at said area of blockage by delivering second ultrasound energy generated by the ultrasound probe to the area of blockage, wherein the delivering causes the microbubbles to activate or rupture.

2. The method of claim 1, comprising using the ultrasound probe that is a probe external to the retinal blood vessel.

3. The method of claim 1, comprising using the ultrasound probe that is an intraocular probe.

4. The method of claim 1, comprising using the ultrasound probe that comprises an ultrasound component and at least one more additional functional component.

5. The method of claim 4, comprising using the ultrasound probe that includes a laser.

6. The method of claim 4, comprising using the ultrasound probe that includes a pulsed-wave Doppler system.

7. The method of claim 4, comprising using the ultrasound probe that includes a cautery.

8. The method of claim 1, further comprising delivering optical treatment to the area of blockage.

9. The method of claim 1, further comprising therapeutic cauterization.

10. The method of claim 1, further comprising measuring blood flow velocity.

11. The method of claim 1, wherein the directing includes supplying the microbubbles via an intravascular injection into a systemic circulation of the patient.

12. The method of claim 1, wherein the directing includes supplying the microbubbles via injection into the eye.

13. The method of claim 12, wherein the supplying includes injecting the microbubbles into a posterior chamber of the eye, an anterior chamber of the eye, or an intraocular tissue.

14. The method of claim 13, wherein said injecting includes injecting the microbubbles subretinally, subchoroidally, intralenticularly, intracorneally, or in the ciliary body.

15. The method of claim 1, wherein the supplying includes applying microbubbles to a surface of the eye.

16. The method of claim 1, wherein the supplying includes delivering the microbubbles into the retinal blood vessel by way of a catheter.

* * * * *